United States Patent
Grimard et al.

(10) Patent No.: US 7,828,803 B2
(45) Date of Patent: Nov. 9, 2010

(54) DEVICE FOR REAMING THE INTRAMEDULLARY CANAL OF A BONE AND A SYSTEM FOR IMPLEMENTING THIS DEVICE

(75) Inventors: Jean-Christophe Grimard, Celettes (FR); Jose Costa, Issy les Moulineaux (FR); Thierry Cousin, Menars (FR)

(73) Assignee: Sferic Stellite, Menars (FR)

( * ) Notice: Subject to any disclaimer, the term of this patent is extended or adjusted under 35 U.S.C. 154(b) by 1126 days.

(21) Appl. No.: 10/943,153

(22) Filed: Sep. 16, 2004

(65) Prior Publication Data

US 2005/0216021 A1 Sep. 29, 2005

(30) Foreign Application Priority Data

Sep. 16, 2003 (FR) .................................. 03 10861

(51) Int. Cl.
*A61B 17/00* (2006.01)
*B24D 15/00* (2006.01)
(52) U.S. Cl. ........................... 606/80; 606/81; 451/493; 451/513; 451/535
(58) Field of Classification Search .................. 606/80, 606/81; 451/493, 513, 535
See application file for complete search history.

(56) References Cited

U.S. PATENT DOCUMENTS

| | | | | |
|---|---|---|---|---|
| 577,582 A | * | 2/1897 | Lane et al. ................... 451/500 |
| 2,038,782 A | * | 4/1936 | Ellis ............................. 51/297 |
| 2,309,456 A | * | 1/1943 | Hoskin et al. ................ 451/535 |
| 2,310,211 A | * | 2/1943 | Brostrom ....................... 69/6.5 |
| 4,000,766 A | * | 1/1977 | Sutcliffe ................... 144/144.1 |
| 4,092,806 A | * | 6/1978 | Wich ........................... 451/237 |
| 5,522,817 A | * | 6/1996 | Sander et al. ................ 606/329 |
| 5,527,316 A | | 6/1996 | Stone et al. .................... 606/80 |
| 5,908,423 A | * | 6/1999 | Kashuba et al. ................ 606/80 |
| 7,241,205 B2 | * | 7/2007 | Toyota et al. .................. 451/44 |
| 2005/0272359 A1 | * | 12/2005 | Pontieri ....................... 451/495 |

FOREIGN PATENT DOCUMENTS

| EP | 0 563 585 A1 | 10/1993 |
|---|---|---|
| EP | 1 174 201 A1 | 1/2002 |

\* cited by examiner

*Primary Examiner*—Thomas C Barrett
*Assistant Examiner*—Sameh Boles
(74) *Attorney, Agent, or Firm*—Perman & Green LLP

(57) ABSTRACT

The present invention concerns a device for reaming the intramedullary canal of a bone, including a body elongated along an axis roughly parallel to the longitudinal axis of the canal, with variable cross section, and of a shape that can cooperate with the inner wall of the intramedullary canal of the bone, characterized in that a helicoidal channel is formed on the body in order to receive a removable and disposable band provided with cutting elements. The present invention also concerns a mounting system for the band onto body of the device.

11 Claims, 5 Drawing Sheets

DEVICE FOR REAMING THE INTRAMEDULLARY CANAL OF A BONE AND A SYSTEM FOR IMPLEMENTING THIS DEVICE

The present invention concerns a device for reaming the intramedullary canal of a bone. The device also concerns a system permitting implementing this device.

BACKGROUND

In joint arthroplasty, regardless of the joint, there are several types of prostheses that differ depending on the pathology to be treated, the health status of the patient, and the type of route and operating technique.

Surgeons wish to adapt the preparation of a bone intramedullary canal as a function of the type of prosthesis that they wish to insert, in order to assure an efficacious and risk-free operation, while guaranteeing the reliability of the implant anchoring.

Medullary sizing is done by means of a reamer. This reamer shapes the intramedullary canal with precision so that the volume obtained corresponds to the volume of the implant to be positioned. For this, the reamer is covered partially or completely with teeth over its outer envelope, and these teeth cut and tamp spongy and cortical bone.

There are different types of teeth, more or less aggressive, which permit the medullary sizing desired by the surgeon, as a function of the type of prosthesis chosen. For these different types of teeth, it is possible to vary the parameters of the teeth: cutting angle, top flat part of the tooth, pitch, orientation of the teeth.

A reamer in the shape of a hollow shaft provided with teeth on its surface is known from patent EP 0 634,145. The reamer comprises a longitudinal slit that gives elasticity to the reamer. One disadvantage of this reamer is that the stresses are concentrated at the bottom of the teeth during reaming of the bone, entailing significant risks of breaking.

This problem is resolved in patent EP 0 563,585 and patent application EP 1,174,201 by helical teeth permitting the stresses to be distributed over the helix formed by the teeth.

Patent EP 0 563,585 discloses a plastic reamer provided with helical teeth with different angles of attack along the reamer, the teeth possibly being divided into two parts along the cutting edge of the reamer. The reamer comprises an inner canal that permits aspiration of bone debris during reaming.

Patent application EP 1,174,201 teaches a reamer provided with teeth positioned in a helix, which is machined into the surface of the reamer body.

One disadvantage of all these reamers is that they are difficult to manufacture, and therefore used for several patients, being cleaned and sterilized between every two patients. However, cleaning reamers is difficult due to the angular shape of the teeth, and in particular the retention zones that make up the teeth, which can lead to a contamination of bone or marrow from one patient to another and therefore to transmission of Kreuzfeld-Jacob-type diseases.

SUMMARY

The object of the present invention is to alleviate certain disadvantages of the prior art by proposing a reamer that is easy to clean and does not comprise a risk of contamination from one patient to another.

This object is attained by a device for reaming the intramedullary canal of a bone, comprising a body elongated along an axis that is roughly parallel to the longitudinal axis of the canal and cutting elements, the elongated body having a variable cross section and a shape designed to cooperate with the inner wall of the intramedullary canal of the bone, characterized in that the cutting elements are positioned on a removable and disposable band wound around the elongated body along a helicoidal channel formed on said body.

According to another particular characteristic, the channel is a rounded threading.

According to another particular characteristic, the band is flexible, so as to mate with the shape of the channel, and in that it comprises at least one catch formed near one end of the band, said catch cooperating with a notch formed near the upper end of the channel to hold the band at the top of the body.

According to one particular characteristic, the band comprises a second catch formed near the other end of the band, said second catch cooperating with a second notch formed near the lower end of the channel in order to hold the band at the bottom of the body.

According to one particular characteristic, a sleeve is screwed onto the lower end of the body in order to hold the band at the bottom of the body.

According to one particular characteristic, the band is glued onto the body by means of a biocompatible adhesive.

According to one particular characteristic, the band is held on the body by an abrasive attached under the band.

According to another particular characteristic, the band is a spring screwed into the channel.

According to another particular characteristic, the width of the band is, at the most, equal to the pitch of the helix, so that once the band is joined to the body, the borders of the band are, at the most, contiguous.

According to another particular characteristic, the cutting elements of the band are made up of one or more lines of teeth.

According to another particular characteristic, the cutting elements of the band are made up of one or more edges, of length roughly equal to the length of the band, each edge at least one cutting plane.

Another object of the invention is to propose a system for mounting the band onto the body of the device.

This object is attained by a system characterized in that it comprises a roughly horizontal axle that can rotate and is mobile along its axis, onto which are mounted, one behind the other, the body of the device as well as the body of a second device serving as a template, the longitudinal axes of the body of the device and the template being more or less aligned with said axle, and in that it also comprises a wheel onto which the band is wound, as well as a digit, mounted fixed in translation relative to the wheel and engaged in the threading of the template, the distance separating the plane of the wheel and the axis of the digit being roughly equal to the distance separating the lower end of the body of the device from that of the template, so that when the template and the body of the device undergo a rotation around the axis of the mounting system, the digit moves along the threading of the template and permits the band to be correctly wound in the threading of the body of the device.

BRIEF DESCRIPTION OF THE DRAWINGS

Other particular characteristics and advantages of the present invention will appear more clearly upon reading the description below, made in reference to the attached drawings, in which.

DETAILED DESCRIPTION

Figure 1:
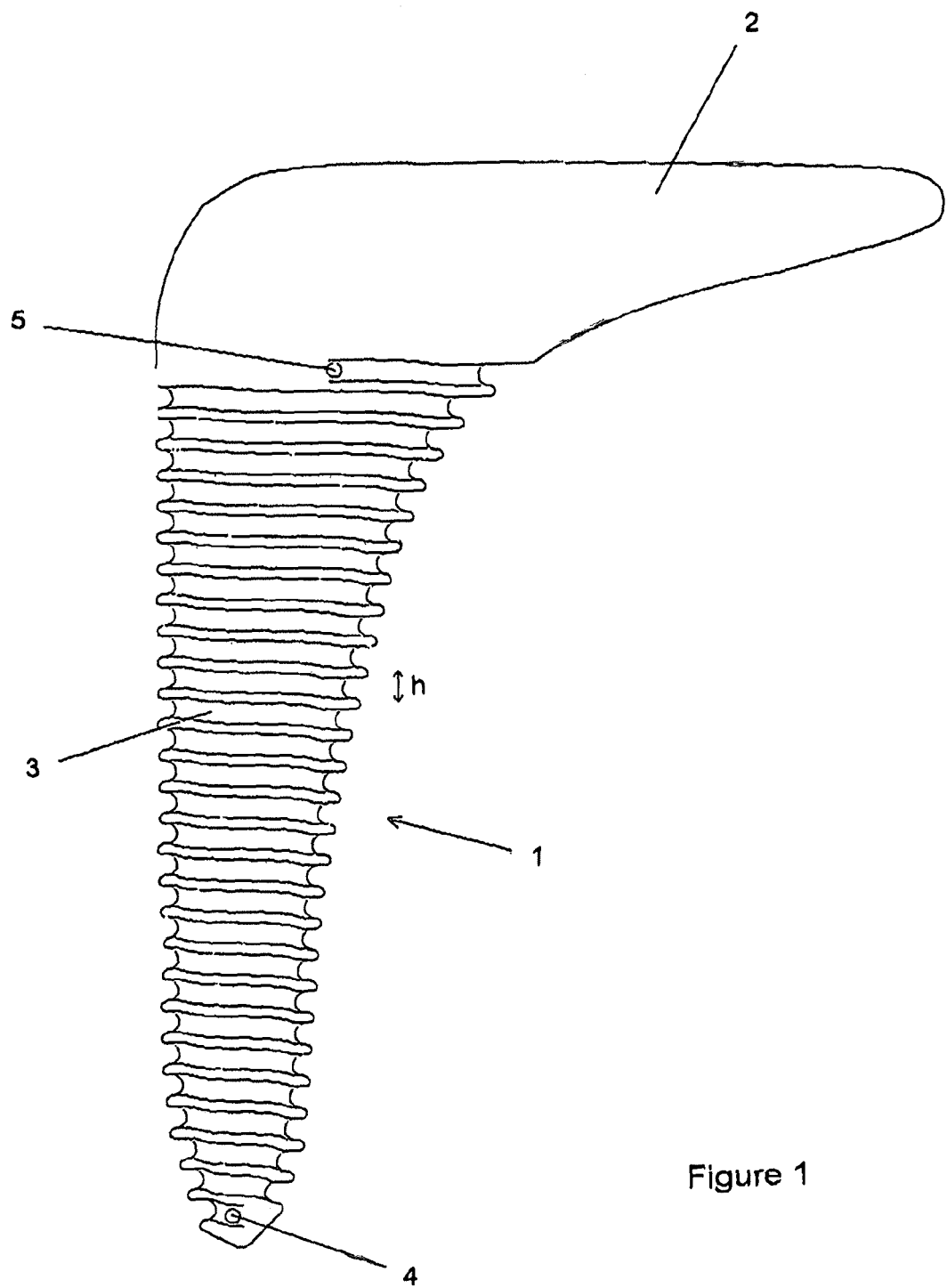
FIG. 1 shows a side view of the reamer without the removable band.

The reamer according to the invention, shown in particular in FIG. 1, is made up of a body (1) and a handle (2). Handle (2) is either soldered on or removable, for example. In the case where it is removable, it may be attached to the upper end of the body of the reamer, for example, by ratcheting. The ratcheting system of the reamer may also receive a test head.

Reamer body (1) is elongated along an axis roughly parallel to the longitudinal axis of the intramedullary canal of the bone to be reamed. It has a variable cross-section permitting it to cooperate with the inner wall of the intramedullary canal of the bone.

Figure 3:
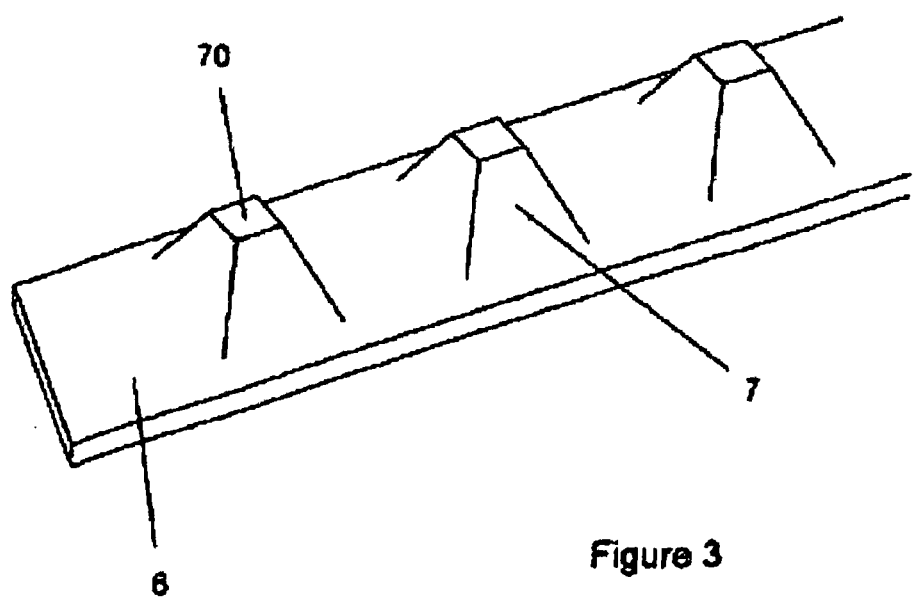
FIG. 3 shows a perspective view of the removable band according to the embodiment of FIG. 2.
Figure 5:
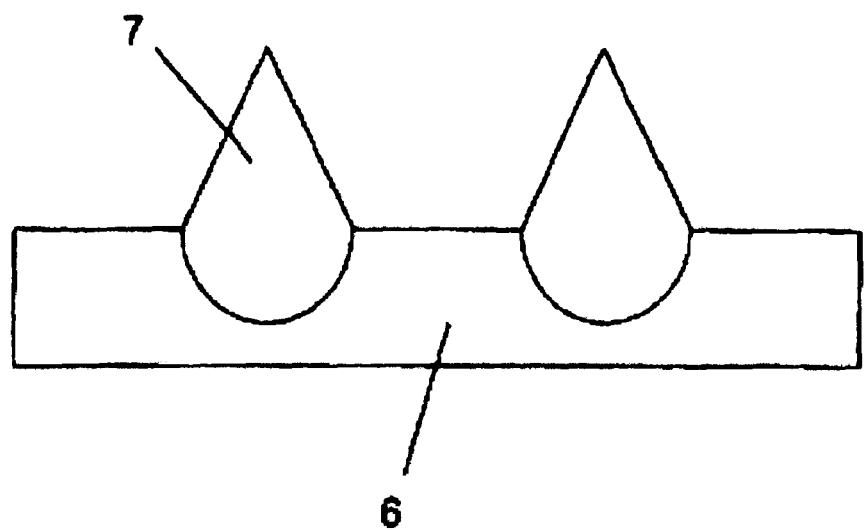
FIGS. 5 and 6 show cross-sectional views of the band according to second and third embodiments, respectively.
Figure 6:
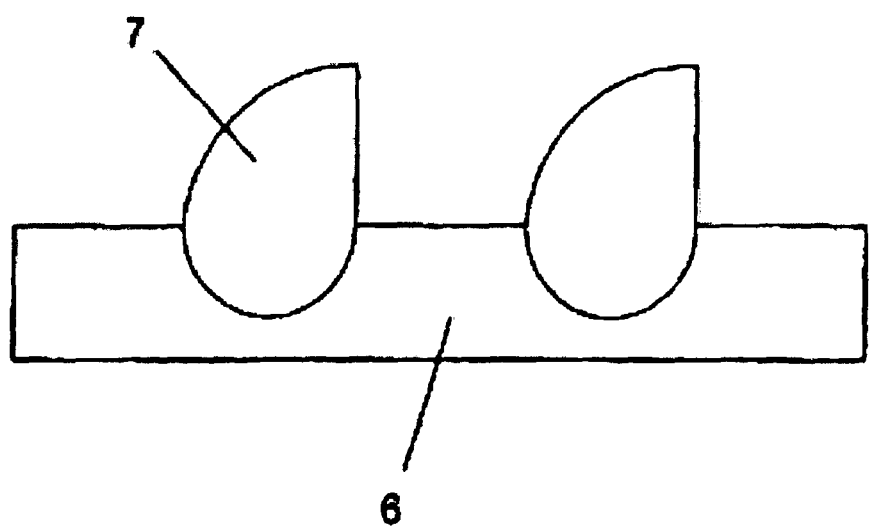

A helical threading (3) is created on reamer body (1) according to the invention, permitting receiving removable band (6) provided with cutting elements (7). This band (6), shown in particular in FIGS. 3, 5 and 6, is made of a flexible material, so as to be able to be wound around reamer body (1). On the other hand, reamer body (1) is rigid, for example made of metal, so as to be able to control the reaming. Cutting elements (7) are created, for example, by stamping or machining. Cutting elements (7) are made up either of one or several edges parallel to each other, each of a length approximately equal to the length of the band, or of one or several lines of teeth, along the length of the band. In this latter case, the geometric characteristics of the teeth are chosen as a function of the type of bone to be reamed or the type of sizing sought.

Figure 2:
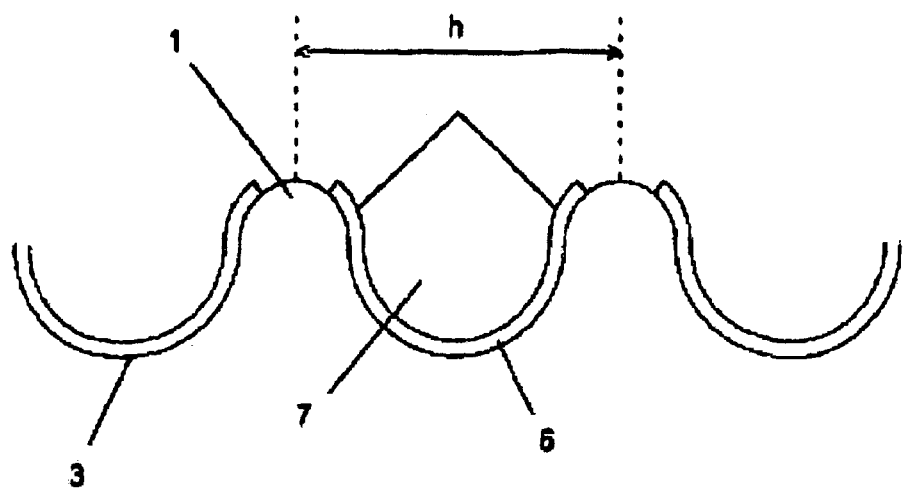
FIG. 2 shows a detail view in longitudinal section of the reamer provided with a removable band according to one embodiment.

Band (6) is mounted on reamer body (1) before the surgical intervention and then is removed and discarded after the intervention. Reamer body (1) is reused after cleaning and sterilization, and then a new band is mounted. The body of the reamer is smooth and threading (3) is rounded, as shown in FIG. 2, which permits easy cleaning, and eliminates the risk of bone debris, blood or marrow remaining adhered on reamer body (1) when the reamer is used for a new patient.

Figure 4:
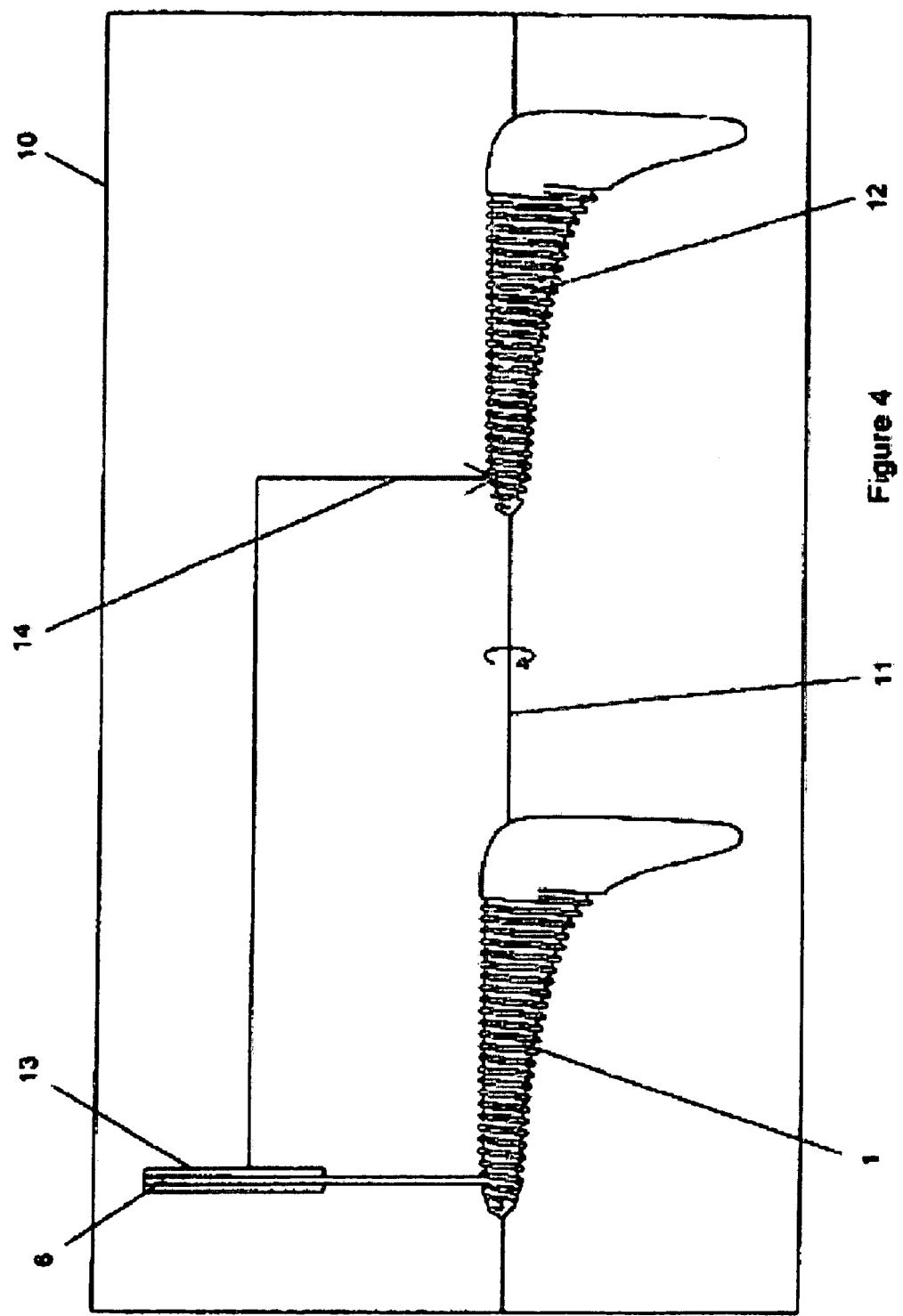
FIG. 4 shows a side view of the system for mounting the band on the reamer.

Band (6) is mounted in threading (3) of reamer body (1), either manually, or by means of a mounting system (10), shown in particular in FIG. 4. This mounting system (10) comprises a more or less horizontal axle (11) that can rotate and is mobile along its axis. Reamer body (1) onto which a band must be mounted, as well as a reamer body serving as a template (12), are mounted one behind the other on this axle (11), so that the longitudinal axis of the reamer body is more or less aligned with said axle (11). Band (6) is wound over a wheel (13) situated above reamer body (1) onto which band (6) must be mounted. A digit (14) mounted fixed in translation relative to wheel (13) is engaged in the threading of template (12), in such a way that the distance separating the plane of wheel (13) and the axis of the digit are roughly equal to the distance separating the lower end of reamer body (1) onto which band (6) must be mounted and the lower end of template (12). Thus, when template (12) and reamer body (1) undergo a rotation around axle (11) of mounting system (10), digit (14) moves along the threading of template (12) and permits band (6) to be correctly wound in the threading of reamer body (1).

The mounting of band (6) onto reamer body (1) begins by ratcheting a first catch (not shown) of the band into an orifice (4, 5) situated near the lower end or upper end, respectively, of threading (3), depending on the direction in which the band will be mounted (from bottom to top or from top to bottom of the reamer body). After band (6) has been mounted in threading (3), a second catch (not shown) is ratcheted into a second orifice (5, 4) situated near the upper end or lower end, respectively, of threading (3).

Figure 7:
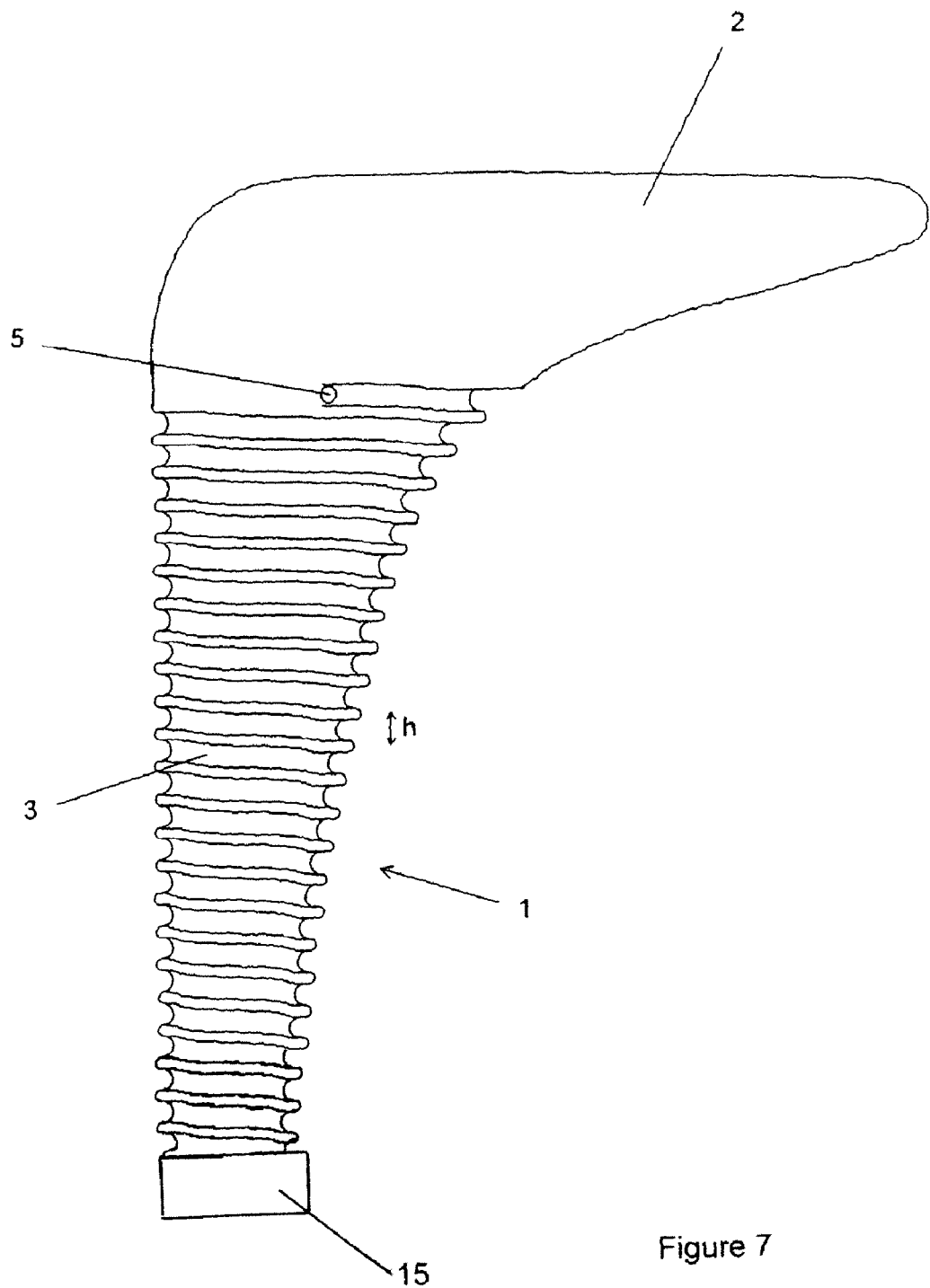
FIG. 7 shows another embodiment as disclosed herein.

In a variant shown in FIG. 7, the reamer body (1) does not comprise a lower orifice (4); in order to hold the lower end of the band (6) on the reamer, a sleeve (15) is screwed onto it's lower end.

In a first embodiment, band (6) is held in threading (3) by gluing by means of a biocompatible adhesive that can be eliminated by heating at a moderate temperature, so as not to damage the reamer body, or with a dissolvent that does not affect reamer body (1).

In a second embodiment, band (6) is held in threading (3) by means of an abrasive attached under band (6). This embodiment has the disadvantage of wearing [the reamer] out more rapidly due to the marks left by the abrasive on the reamer body.

In these first two embodiments, the band is mounted onto the reamer body by means of mounting system (10) of the present invention.

In a third embodiment, the band is metal as well as elastic and acts as a spring. In this case, the band is not wound by means of mounting system (10) described above, but is simply screwed into the threading starting from the lower end of the reamer body. In this case as well, the band is held by ratcheting catches into orifices (4, 5) of the reamer body.

The helical pitch (h) of threading (3) is, for example, comprised between 1 mm and 5 mm. The width of band (6) is, at most, equal to helical pitch (h), so that the borders of the band are at most contiguous, but do not overlap.

Each reamer body (1) can receive bands provided with more or less aggressive cutting elements (7). Thus, in the embodiment of FIG. 3, cutting elements (7) are made up, as shown in FIG. 3, of pyramidal teeth that have an opening (70) at the level of their apex in order to be able to release pressure during reaming so as to prevent a fatty embolism. In the embodiment of FIGS. 5 and 6, the cutting elements are made up of edges created over more or less the entire length of the band. Each of the edges shown in FIG. 5 has two cutting planes, permitting reaming the bone in both directions during a back-and-forth movement of the reamer. In contrast, each of the edges shown in FIG. 6 only has one cutting plane, the other side of the edge being rounded. This latter embodiment therefore does not permit reaming the bone in both directions.

It should be clear, for persons skilled in the art, that the present invention permits embodiments under numerous other specific forms without exceeding the field of application of the invention as claimed. Consequently, the present embodiments should be considered by way of illustration, but can be modified in the field and are defined by the scope of the attached claims; also, the invention must not be limited to the details given above. Thus, the band can be provided with all types of cutting elements commonly used to ream a bone.

The invention claimed is:

1. A mounting system for mounting band onto a body, comprising: a reaming device comprising: a rigid body having a variable cross-section and a shape to cooperate with the inner wall of the intramedullary canal of the bone so as to be elongated along an axis roughly parallel to the longitudinal axis of the canal to be reamed; a template comprising a rounded helical channel is formed on said body; a removable and disposable band, wherein said band is made of flexible material so as to be able to be wound: cutting elements positioned on the removable and disposable band wound around said elongated body along the helical channel formed on said body), said cutting elements being manufactured by stamping and machining of the band and said band being mounted on the body of the device before the surgical intervention and then removed and discarded after the surgical intervention; and a mounting device comprising: a roughly horizontal axle arranged to rotate and which is mobile along its axis, said horizontal axle being arranged to cooperate with the body of the device, and with a body of a device serving as the template so that the body of the device and the body of the device serving as the template are mounted one behind the other on the horizontal axle of the mounting device and that the longitudinal axes of the bodies of the device and the template are roughly aligned with said horizontal axle; a wheel onto which said band is wound; and a digit mounted fixed in translation relative to said wheel and engaged in the helical channel of the template, wherein the distance separating wheel and digit is roughly equal to the distance separating the lower end of the body of the device from that of the template, so that when the template and the body of the device undergo a rotation around the horizontal axle of said mounting system, the digit moves along the helical channel of the template and the band is correctly wound in the helical channel of the body of the device.

2. The mounting system according to claim 1, wherein said channel is a rounded threading.

3. The mounting system according to claim 1, wherein said flexible band is able to mate with the shape of channel, and comprises at least one catch arranged near one end of the band to cooperate with an orifice formed near the upper end of channel in order to hold the band at the top of the body.

4. The mounting system according to claim 3, wherein said band comprises a second catch arranged near the other end of the band to- cooperate with a second orifice formed near the lower end of channel in order to hold band at the bottom of the body.

5. The mounting system according to claim 3, wherein a sleeve is screwed onto the lower end of body to hold band at the bottom of the body.

6. The mounting system according to claim 1, wherein said band is glued onto the body by means of a biocompatible adhesive.

7. The mounting system according to claim 1, wherein said band is held onto the body by an abrasive attached under the band.

8. The mounting system according to claim 1, wherein said band is a spring screwed into channel.

9. The mounting system according to claim 1, wherein the width of band is, at the most, equal to the helical pitch, so that once band is joined to the body, the borders of the band are, at the most, contiguous.

10. The mounting system according to claim 1, wherein said cutting elements of the band include one or several rows of teeth.

11. The mounting system according to claim 1, wherein said cutting elements of the band include one or several edges arranged, roughly over the entire length of the band, each edge having at least one cutting plane.

* * * * *

UNITED STATES PATENT AND TRADEMARK OFFICE
CERTIFICATE OF CORRECTION

| | | |
|---|---|---|
| PATENT NO. | : 7,828,803 B2 | Page 1 of 1 |
| APPLICATION NO. | : 10/943153 | |
| DATED | : November 9, 2010 | |
| INVENTOR(S) | : Jean-Christophe Grimard et al. | |

It is certified that error appears in the above-identified patent and that said Letters Patent is hereby corrected as shown below:

Col. 5, Claim 1, Line 5, delete "body)," and insert -- body, --, therefor.

Signed and Sealed this
Eighth Day of February, 2011

David J. Kappos
*Director of the United States Patent and Trademark Office*